United States Patent [19]
Josefsen

[11] Patent Number: 5,195,505
[45] Date of Patent: Mar. 23, 1993

[54] SURGICAL RETRACTOR

[75] Inventor: Turi Josefsen, Westport, Conn.

[73] Assignee: United States Surgical Corporation, Norwalk, Conn.

[21] Appl. No.: 634,482

[22] Filed: Dec. 27, 1990

[51] Int. Cl.$^5$ .................................................. A61B 17/02
[52] U.S. Cl. ...................................... 128/20; 606/198
[58] Field of Search ................ 128/20, 17; 606/191, 606/198

[56] References Cited

U.S. PATENT DOCUMENTS

| | | |
|---|---|---|
| 972,983 | 10/1910 | Arthur . |
| 1,244,741 | 10/1917 | McCleary . |
| 1,328,624 | 1/1920 | Graham . |
| 2,202,748 | 5/1940 | Solo .................................... 128/20 |
| 2,816,552 | 12/1957 | Hoffman . |
| 3,313,294 | 4/1967 | Uddenberg . |
| 3,467,079 | 9/1969 | James . |
| 4,130,113 | 12/1978 | Graham ............................... 128/20 |
| 4,190,042 | 2/1980 | Sinnreich . |
| 4,226,228 | 10/1980 | Shin et al. . |
| 4,459,978 | 7/1984 | Kotsanis . |
| 4,654,028 | 3/1987 | Suma . |
| 4,765,311 | 8/1988 | Kulik et al. . |
| 4,909,789 | 3/1990 | Taguchi et al. ..................... 606/198 |
| 5,113,846 | 5/1992 | Hiltebrandt et al. ................ 128/20 |

FOREIGN PATENT DOCUMENTS

| | | | |
|---|---|---|---|
| 1251888 | 8/1986 | U.S.S.R. | ............................... 606/191 |
| 1360708 | 12/1987 | U.S.S.R. | ............................... 128/20 |
| 736949 | 5/1990 | U.S.S.R. | ............................... 606/198 |

Primary Examiner—John G. Weiss
Attorney, Agent, or Firm—Thomas R. Bremer; Peter G. Dilworth; Rocco S. Barrese

[57] ABSTRACT

A surgical retractor is provided having an elongated tubular structure with a proximal and distal end. A plurality of interleaved retractor blades are pivotally mounted in a distal end of the tubular housing and are movable between a closed position wherein the blades are in stacked relation and an open position wherein the blades are deployed in an interleaved fan configuration. Various structure is provided on the tubular housing to move the blades between an open and closed position.

24 Claims, 3 Drawing Sheets

FIG. 5

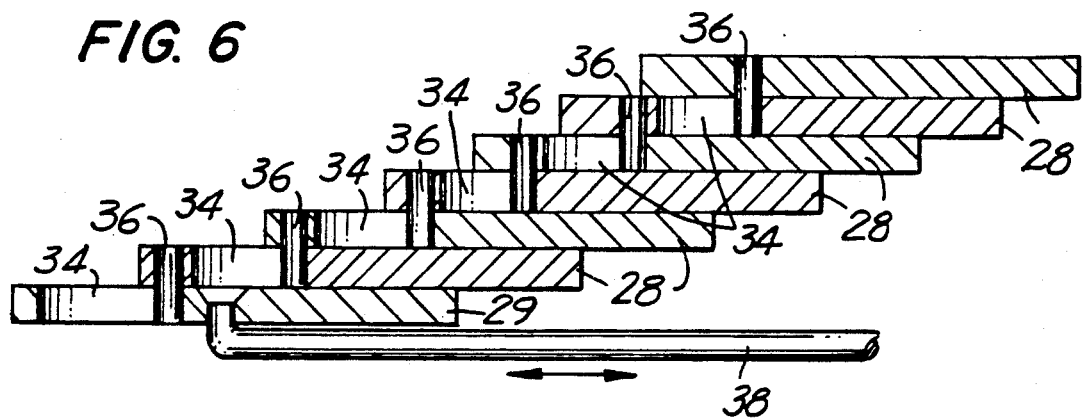
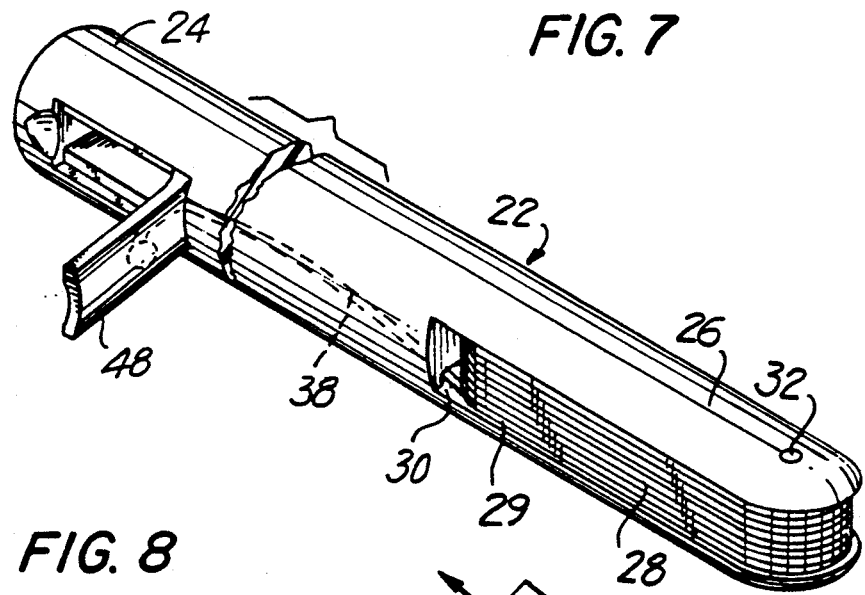
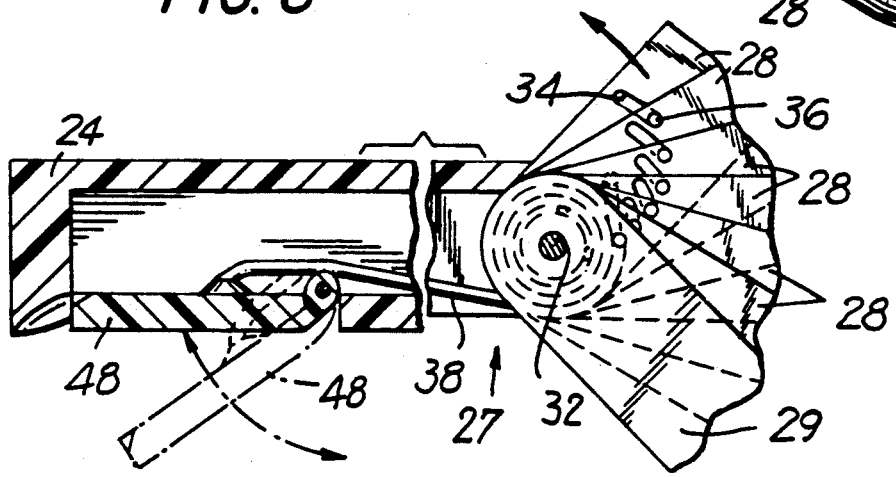

SURGICAL RETRACTOR

BACKGROUND OF THE INVENTION

1. Field of the Invention

This invention relates generally to surgical instrumentation and, more particularly, to a retractor adapted for use with endoscopic or laparascopic devices commonly used for performing examinations or surgical procedures within body cavities.

2. Description of the Prior Art

Endoscopic or laparascopic procedures are characterized by the provision of an elongated cannula structure having a relatively thin diameter with a proximal and distal end. The distal end is passed through the surrounding tissue into the body cavity wherein the surgical procedure or examination is to be effected, thus providing a conduit for the insertion of surgical instrumentation. A plurality of cannula structures may be used to allow operation of a variety of instruments simultaneously during a given procedure. For example, one cannula may provide a conduit for an endoscope for vision and illumination within the operative cavity while other cannulas provide conduits for control of specialized surgical instruments designed for performing specific procedural functions.

In conventional surgical procedures the function of holding tissue and organs in a given location to facilitate access and viewing is accomplished by a retractor. This instrument is ordinarily in the form of a broad paddle structure or multiple fingers attached to a handle. See, for example, U.S. Pat. No. 3,467,079 (James) This structure however, is not usable in laparascopic procedures since the retractor is too large to be inserted through the cannula structure into the operative body cavity.

Collapsible intralumen expanders or retractors have taken the form of radial fingers which are activatable to extend relative to each other upon entering the body cavity. See, for example, U.S. Pat. Nos. 4,654,028 (Suma), 4,459,978 (Kotsanis). Dilators of this type are also known. See, e.g., U.S. Pat. Nos. 1,328,624 (Graham) and 972,983 (Arthur). In each case, once the retractive or dilatory function is completed, the fingers are compressed and withdrawn. Another collapsible retractor structure includes a pair of collapsible fingers joined by a web of resilient material which, upon insertion into the cannula structure, can expand to form a retractive structure. See, for example, U.S. Pat. No. 4,190,042 (Sinnreich).

Such collapsible structures have certain inherent drawbacks associated therewith. For example, upon retraction loose tissue may become caught within the fingers and cause unintentional trauma to retracted tissue. Also, where the tissue is not readily dislodged, collapsing and withdrawing the retractor may be difficult and complicated.

SUMMARY OF THE INVENTION

Accordingly, it is an object of the present invention to provide a surgical retractor which overcomes the drawbacks associated with prior art retractors.

Another object of the present invention is to provide a surgical retractor adapted for use in endoscopic and laparascopic procedures.

A further object of the present invention is to provide a surgical retractor which is deployable within the body cavity to provide a retractive function therein.

Briefly stated, the invention resides in the provision of a surgical retractor having an elongated tubular structure with a proximal and distal end. A plurality of interleaved retractor blades are pivotally mounted in a distal end of the tubular housing and are movable between a closed position wherein the blades are in stacked relation and an open position wherein the blades are deployed in an interleaved fan configuration. Means are provided on or associated with the tubular housing to move the blades between an open and closed position.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 6 is a partial side view taken along line 6—6 of FIG. 5.

FIG. 7 is a perspective view of a laparascopic retractor in accordance with another embodiment of the present invention.

FIG. 8 is a plan view in cross-section of the retractor of FIG. 7.

DESCRIPTION OF PREFERRED EMBODIMENTS

Figure 1:
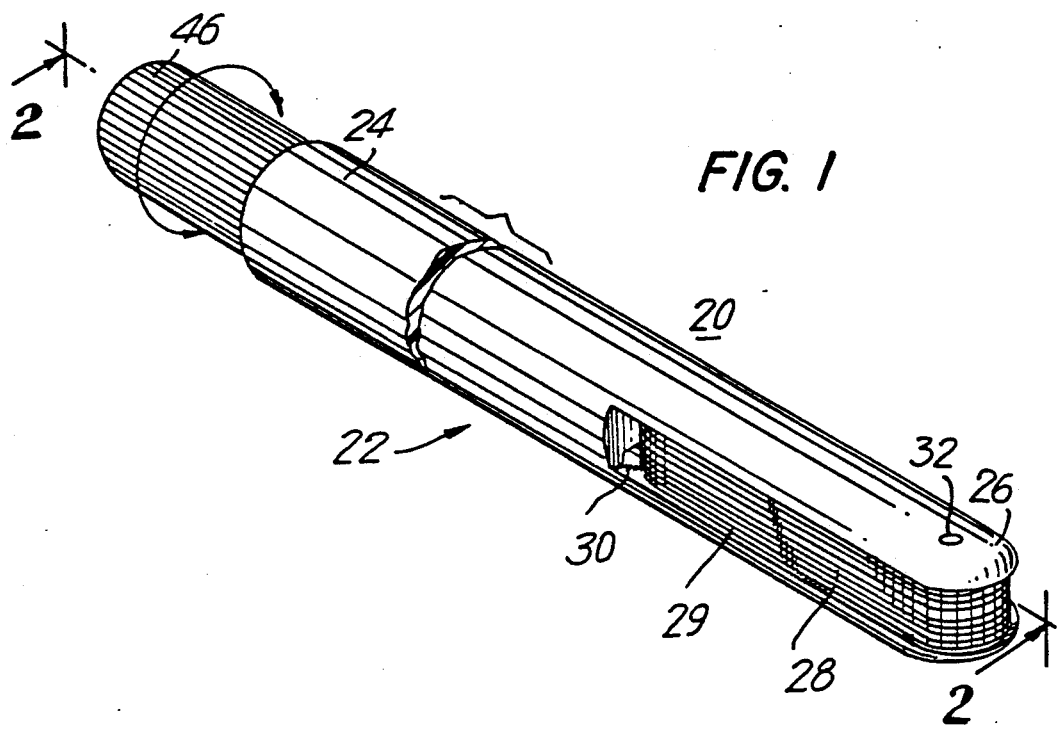
FIG. 1 is a perspective view of a laparascopic retractor in accordance with one embodiment of the present invention.
Figure 2:
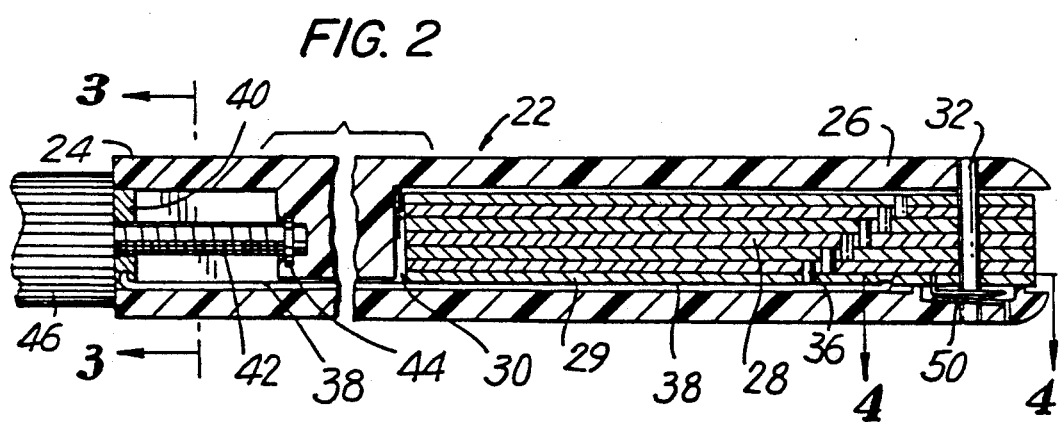
FIG. 2 is a side view in cross-section taken along line 2—2 of the embodiment of FIG. 1.
Figure 3:
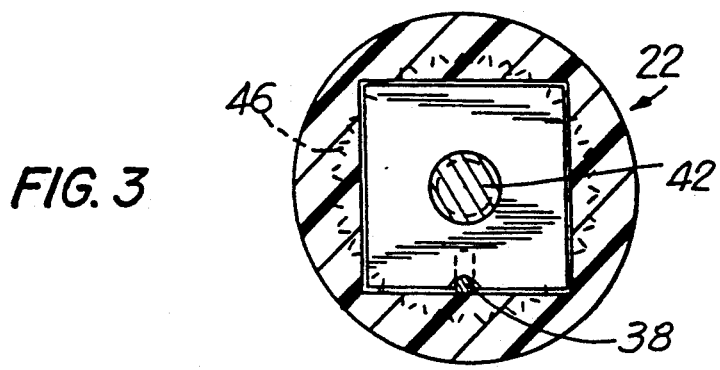
FIG. 3 is a frontal view taken along line 3—3 in FIG. 2.
Figure 4:
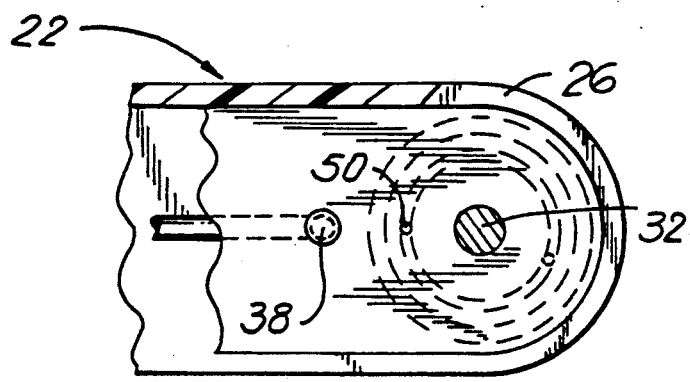
FIG. 4 is a partial plan view taken along line 4—4 in FIG. 2.

Referring now to the drawings and in particular to FIG. 1, there is shown a surgical retractor in accordance with one embodiment of the present invention. The retractor, generally indicated by 20 is in the form of an elongated tubular housing 22 having a proximal end 24 and a distal end 26. This embodiment is particularly well adapted for use in endoscopic or laparoscopic procedures and is preferably dimensioned to be deployable through a tubular cannula structure, e.g., of 5 mm or 10 mm internal diameter.

Figure 5:
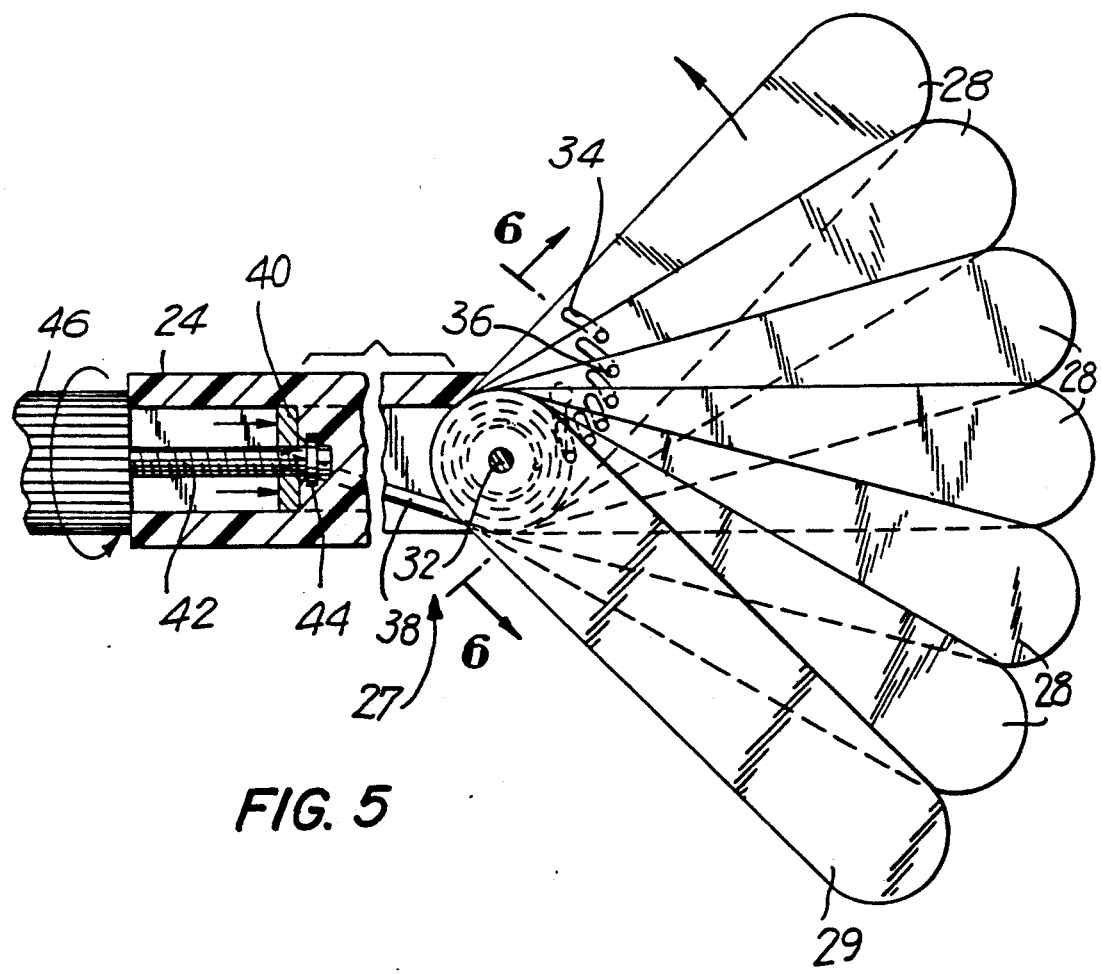
FIG. 5 is a plan view in partial cross-section showing the deployed retractor blades of the embodiment of FIG. 1.

Retractor assembly 27 comprises a plurality of stacked interleaved retractor blades 28 disposed in cavity 30 formed in the distal end 26 of the elongated tubular housing 22. The retractor blades 28 are pivotal relative to housing 22 through pivot pin 32. The blades each have an arcuate slot 34 and pin 36 configuration with a pin 36 of a first blade 28 fitting within the arcuate slot 34 of an adjacent blade 28 to allow for controlled deployment of the interleaved retractor blades 28 into a fan configuration. See FIG. 5.

In the embodiment of FIGS. 1–6, deployment and retraction of the interleaved retractor blades 28 is effected by reciprocal longitudinal motion of flexible rod 38 connected to lower retraction blade 29. This rod 38 extends through the elongated tubular housing 22 from the lower retractor blade 29 of the stack to disk 40. Threaded shaft 42 is rotatably connected to the proximal end 24 of the elongated tubular housing 22 by flange 44. Rotation is accomplished by knob 46 and, for endoscopic and laparascopic applications, retractor 20 is adapted to permit all or part of knob 46 to remain outside the body cavity for easy manipulation. Disk 40 is threaded onto shaft 42 such that rotation of knob 46 causes disk 40 to move longitudinally along the axis of the elongated tubular housing 22. As disk 40 moves distally (FIG. 5), rod 38 causes the stacked interleaved retractor blades 28 to deploy into a fan configuration.

Preferably, the retractor blades will deploy to a semicircular configuration extending from about the 9 o'clock position to about the 3 o'clock position. Where less retractive area is desired, the retractor blades may be configured to deploy to a semicircular configuration extending from about the 11 o'clock position to about the 1 o'clock position. Similarly, opposite rotation of knob 46 causes the deployed retractor blades to collapse into a stacked configuration within cavity 30 of tubular housing 22.

Referring now to FIGS. 7–8, there is shown a second embodiment of a laparascopic retractor in accordance with the present invention. Operation of this embodiment is substantially the same as that described above with respect to the first embodiment with the exception of the means for moving the blades 28 between the open and closed position. In this embodiment flexible rod 38 extends from lower blade 29, through elongated tubular housing 22 to pivotal tab 48 mounted on the proximal end 24 of housing 22. When tab 48 is extended from housing 22 (FIG. 7) rod 38 moves longitudinally proximally such that the stacked interleaved retractor blades 28 are retained within cavity 30 in the distal end 26 of tubular housing 22. As tab 48 is pivoted into the proximal end 24 of housing 22, flexible rod 38 is moved longitudinally distally to deploy the interleaved retractor blades 28 to the fanned configuration. See FIG. 8. Where desired, spring 50 may be positioned around pivot pin 32 and connected to a lower blade 29 of the retractor assembly 27 to assist in holding the blades in either the open or closed position.

All of the elements of the present invention may be made from a suitable sterilizable surgical material or combination of materials such as stainless steel, aluminum, titanium or an engineering plastic.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A surgical retractor comprising:
   an elongated housing having a proximal and distal end;
   a retractor assembly having a plurality of interleaved retractor blades pivotally attached to the distal end of said housing and controllably positionable between a closed position wherein said blades are in stacked relation, a second position wherein said blades are partially deployed and an open position wherein said blades are deployed in an interleaved fan configuration; and
   means associated with said housing for remotely moving said blades between said closed, said second and said open position from adjacent said proximal end of said housing.

2. A surgical retractor as in claim 1 wherein said means for moving said blades includes a flexible rod attached to at least one of said blades and longitudinally movable within said housing to deploy and close the retractor assembly.

3. A surgical retractor as in claim 2 wherein said flexible rod is attached to a blade of said retractor assembly and a disk threaded onto a threaded shaft such that rotation of the threaded shaft results in longitudinal motion of the disk.

4. A surgical retractor as in claim 2 wherein said flexible rod is attached to a blade of said retractor assembly and a pivotable flap on said housing such that reciprocal movement of said flap results in longitudinal movement of said flexible rod to alternately deploy and close said retracted assembly.

5. A surgical retractor as in claim 1 wherein said retractor blades are provided with at least one slot and at least one pin which interfit into adjacent blades for controlled deployment into a fan configuration.

6. A surgical retractor as in claim 5 wherein said fan configuration extends in the open position within the range of from about the 9 o'clock position to about the 3 o'clock position.

7. A surgical retractor as in claim 1 wherein said blades are attached at a common pivot point.

8. A surgical retractor comprising;
   an elongated tubular housing having a cavity formed in a distal end thereof;
   a retractor assembly having a plurality of interleaved retractor blades pivotally attached to the distal end of said housing and each blade being movably attached to an adjacent blade for controlled angular movement between a closed position wherein said blades are disposed in stacked relation within said cavity, a second position wherein said blades are at least partially deployed, and an open position wherein said blades are fully deployed in an interleaved fan configuration; and
   means associated with said housing for remotely moving said blades between said closed, said second and said open position from adjacent said proximal end of said housing.

9. A surgical retractor as in claim 8 wherein said interleaved fan configuration in the open position extends within the range of from about 9 o'clock position to about the 3 o'clock position.

10. A surgical retractor as in claim 9 wherein the interleaved fan configuration in the open position extends from about the 11 o'clock position to about the 1 o'clock position.

11. A surgical retractor as in claim 8 further comprising means to assist in maintaining the interleaved retractor blades in the fan configuration when open.

12. A surgical retractor as in claim 11 wherein said means to assist comprises a spring.

13. A surgical retractor as in claim 8 wherein said means for moving said blades comprises a longitudinally reciprocally movable rod attached at a distal end to at least one of said retractor blades and attached at a proximal end to means for moving said rod reciprocally longitudinally between an one position and a closed position.

14. A surgical retractor as in claim 13 wherein said means for moving said rod comprises:

a disk having a threaded bore and attached to the proximal end of said rod; and a threaded rod engaging the threaded bore of the disk such that rotation of said rod in a first direction causes said disk to move longitudinally distally with respect to the housing and rotation in the opposite direction causes said disk to move longitudinally proximally with respect to the housing.

15. A surgical retractor as in claim 13 wherein said means for moving said rod comprises a tab attached to the proximal end of the rod and being pivotal between a first position and second position wherein pivotal movement of the tab causes longitudinal reciprocal motion of the rod.

16. A surgical retractor as in claim 8 wherein said blades are attached at a common pivot point.

17. A surgical retractor comprising:
an elongated tubular housing having a proximal and distal end, said distal end being further provided with a longitudinal cavity therein;
a retractor assembly having a plurality of interleaved retractor blades dimensioned to fit within said longitudinal cavity and pivotally attached proximate the distal end of said housing, each blade of said assembly being slidably attached to an adjacent blade for predetermined angular movement, said assembly being movable between a closed position wherein said blades are disposed entirely within said longitudinal cavity in stacked relation and an open position wherein said blades are deployed in an interleaved fan configuration; and
means attached to said housing for moving said retractor assembly between said closed and open position.

18. A surgical retractor comprising:
an elongated housing having a proximal and distal end; p1 a retractor assembly having a plurality of interleaved blades pivotally attached at a common pivot point adjacent to the distal end of said housing and movable between a closed position wherein said blades are in stacked relation and an open position wherein said blades are deployed in an interleaved fan configuration; and
means associated with said housing for remotely moving said blades between said closed and said open position from adjacent said proximal end of said housing.

19. A surgical retractor as in claim 18 wherein said means for moving said blades comprises a shaft connected at a distal end thereof to at least one of said blades and having a threaded portion engagable with rotation means to effect coaxial motion of said shaft.

20. A surgical retractor as in claim 18 wherein said retractor assembly is controllably positionable between said closed position, a second position wherein said blades are partially deployed, and said open position.

21. A surgical retractor comprising:
an elongated housing having a proximal and distal end;
a retractor assembly having a plurality of interleaved retractor blades pivotally attached to the distal end of said housing and movable between a closed position wherein said blades are in stacked relation and an open position wherein said blades are deployed in an interleaved fan configuration; and
means associated with said housing for controllably deploying said blades between said closed and said open position from adjacent said proximal end of said housing.

22. A surgical retractor as in claim 21 wherein said means for controllably deploying said blades comprises a shaft connected at a distal end thereof to at least one of said blades and being controllably coaxially movable in a longitudinal direction with respect to said housing to controllably deploy said blades.

23. A surgical retractor as in claim 22 wherein said shaft includes a threaded portion engagable with rotation means associated with said retractor for controllably moving said shaft coaxially in response to rotation of said rotation means.

24. A surgical retractor comprising:
an elongated housing having a proximal and distal end;
a retractor assembly having a plurality of interleaved retractor blades pivotally attached to the distal end of said housing and movable between a closed position wherein said blades are in stacked relation and an open position wherein said blades are deployed in an interleaved fan configuration; and
rotatable means associated with said housing for remotely deploying said blades between said closed and said open position from adjacent said proximal end of said housing.

* * * * *